(12) United States Patent
Sagae et al.

(10) Patent No.: US 11,523,878 B2
(45) Date of Patent: Dec. 13, 2022

(54) HANDPIECE-TYPE HIGH-FREQUENCY VIBRATION CUTTING DEVICE

(71) Applicant: MICRON MACHINERY CO., LTD., Yamagata (JP)

(72) Inventors: Mohee Sagae, Yamagata (JP); Satoshi Kobayashi, Yamagata (JP); Yoshihiro Minagawa, Yamagata (JP); Hiroki Suzuki, Yamagata (JP); Norihiko Nakajima, Yamagata (JP)

(73) Assignee: Micron Machinery Co., Ltd., Yamagata (JP)

( * ) Notice: Subject to any disclaimer, the term of this patent is extended or adjusted under 35 U.S.C. 154(b) by 425 days.

(21) Appl. No.: 16/615,334

(22) PCT Filed: Sep. 21, 2018

(86) PCT No.: PCT/JP2018/035049
§ 371 (c)(1),
(2) Date: Mar. 23, 2020

(87) PCT Pub. No.: WO2019/097840
PCT Pub. Date: May 23, 2019

(65) Prior Publication Data
US 2020/0214795 A1 Jul. 9, 2020

(30) Foreign Application Priority Data
Nov. 14, 2017 (JP) .............................. JP2017-219015

(51) Int. Cl.
A61C 1/07 (2006.01)
A61B 17/32 (2006.01)
(Continued)

(52) U.S. Cl.
CPC ........ A61C 1/07 (2013.01); A61B 17/320068 (2013.01); A61B 2017/00115 (2013.01); A61B 2017/00172 (2013.01); A61C 3/03 (2013.01)

(58) Field of Classification Search
CPC ........... A61C 1/07; A61C 1/0015; A61C 3/03; A61C 8/0089; A61B 17/320068;
(Continued)

(56) References Cited

U.S. PATENT DOCUMENTS 4,343,111 A 8/1982 Inoue
4,827,911 A 5/1989 Broadwin et al.
(Continued)

FOREIGN PATENT DOCUMENTS

EP 3240609 A1 11/2017
JP S55-101356 A 8/1980
(Continued)

OTHER PUBLICATIONS

Extended European Search Report dated Nov. 24, 2020 issued in the corresponding European patent application No. 18879181.8.

*Primary Examiner* — Brooke Labranche
(74) *Attorney, Agent, or Firm* — Carrier Blackman & Associates, P.C.; Joseph P. Carrier; Fulchand P. Shende

(57) ABSTRACT

A handpiece-type high-frequency vibration cutting device includes a housing (10); a vibration device (21); a holding member (11); a tool (12); and a controller (20) to control the operations of the vibration device (21). The controller (20) controls the vibration of the tool (12) due to the vibration device (21) such that the vibration is burst oscillation in which vibration and stop of vibration are repeated. The controller (20) also controls the entire burst frequency f1 of the tool (12) to be included in the range of 1 to 8 [Hz], one cycle of the burst frequency f1 including a burst period with the holding member (11) vibrating and a stop period with the (Continued)

tool (12) not vibrating. The controller (20) also controls the vibration frequency f2 of the tool (12) during the burst period such that the vibration frequency f2 is in the range of 20 to 60 [kHz].

4 Claims, 6 Drawing Sheets

(51) Int. Cl.
     *A61C 3/03*           (2006.01)
     *A61B 17/00*         (2006.01)

(58) Field of Classification Search
     CPC .............. A61B 17/22012; A61B 17/32; A61B 2017/00115; A61B 2017/00172
     See application file for complete search history.

(56) References Cited

U.S. PATENT DOCUMENTS

| | | |
|---|---|---|
| 8,002,783 B2 | 8/2011 | Vercellotti et al. |
| 2003/0003418 A1 | 1/2003 | Kumabe |

FOREIGN PATENT DOCUMENTS

| | | |
|---|---|---|
| JP | H06-209954 A | 8/1994 |
| JP | H07-106208 B2 | 11/1995 |
| JP | 2001-204735 A | 7/2001 |
| JP | 3553486 B2 | 8/2004 |
| WO | 2016/126793 A1 | 8/2016 |

FIG.3

| BURST FREQUENCY [Hz] | 0.1 | 0.5 | 1 | 2 | 3 | 4 | 5 | 6 |
|---|---|---|---|---|---|---|---|---|
| CUTTING FEELING | × | ○ | ◎ | ◎ | ◎ | ◎ | ○ | ○ |
| FULLY-STOPPED CUTTING FEELING | × | △ | ○ | ○ | ○ | ○ | ○ | ○ |

| BURST FREQUENCY [Hz] | 7 | 8 | 9 | 10 | 11 | 12 | 13 | 14 |
|---|---|---|---|---|---|---|---|---|
| CUTTING FEELING | ○ | ○ | △ | △ | △ | △ | × | × |
| FULLY-STOPPED CUTTING FEELING | ○ | ○ | ○ | ○ | ○ | ○ | ○ | ○ |

COMPARATIVE EXAMPLE

COMPARATIVE EXAMPLE

COMPARATIVE EXAMPLE

HANDPIECE-TYPE HIGH-FREQUENCY VIBRATION CUTTING DEVICE

TECHNICAL FIELD

The present invention relates to a high-frequency vibration cutting device that can efficiently cut an object with high-frequency vibration being transmitted to a cutting tool, for example, attached to a handpiece.

BACKGROUND ART

A handpiece-type high-frequency vibration cutting device has been proposed, the cutting device including a vibration device mounted on a tongue inside a handpiece to therewith vibrate the tongue to thereby vibrate a cutting tool attached to the tongue at a high frequency, so that efficiency in cutting processing and accuracy in processing can be improved (refer to, for example, Patent Literature 1 and Patent Literature 2).

CITATION LIST

Patent Literatures

Patent Literature 1: Japanese Patent Application Laid-Open No. 2001-204735
Patent Literature 2: Japanese Patent No. 3553486

SUMMARY OF INVENTION

Technical Problem

With a high-frequency vibration cutting device disclosed in Patent Literature 1, in cutting bone tissues in an oral surgery, for example, a cutting tool is vibrated by a vibration device with high-frequency vibration, vibration modulated into having a low frequency, or a series of low-frequency burst vibrations. As bone tissues are accurately cut with high-frequency vibration and energy due to vibration of the cutting tool is discharged with modulation into a series of low frequency burst vibrations, the heat generated in soft tissues can be minimized.

A device for dynamic anesthetic and affected part separation disclosed in Patent Literature 2 includes a supersonic oscillator that produces supersonic vibration at 20 to 100 [kHz] and a low-frequency oscillator that produces low-frequency vibration. When it is expected that application of a force into a lesion contact is required in a modulation operating state in which low-frequency vibration is applied in addition to supersonic vibration under an operating state in which only a supersonic oscillator is operating for dynamic anesthetic, periodontal ligament is cut with low-frequency vibration to facilitate separation of tooth germ from alveolar bone, so that an affected part can be separated without application of a large force to the lesion contact and suspension of the supersonic vibration.

In cutting processing of an object in an oral surgery, however, it is preferable, in order to improve the operability of a high-frequency vibration cutting device, that an operator checks by sense of feel the amount of cutting, or how much cutting has been made so far, based on a feeling of cutting strokes, in addition to accurate cutting of bone tissues with high-frequency vibration and minimization of heat generated due to a series of low-frequency vibrations, as disclosed in Patent Literature 1, and cutting of periodontal ligament with low-frequency vibration to facilitate separation of tooth germ from alveolar bone, as disclosed in Patent Literature 2.

In view of the above, the present invention aims to provide a handpiece-type high-frequency vibration cutting device that can improve its operability by having an operator cut while checking the amount of cutting, or how much cutting has been made so far, from a feeling of cutting strokes.

Solution to Problem

[1] In order to achieve the above-described object, a handpiece-type high-frequency vibration cutting device according to the present invention includes a housing; a vibration device mounted on the housing; a tool mounted on the vibration device; and a controller configured to control the operation of the vibration device to thereby cause the tool to vibrate in a direction of the axial line of the vibration device, wherein the controller controls the vibration of the tool, the vibration being caused by the vibration device, such that the vibration is burst oscillation in which vibration and stop of vibration are repeated, and the controller controls the burst frequency $f_1$ of the tool such that the burst frequency $f_1$ as a whole is included in the range of 1 to 8 [Hz], one cycle of the burst frequency $f_1$ including a burst period with the tool vibrating and a stop period with the tool not vibrating, a duty ratio $d_1$ obtained by dividing the pulse width $t_1$ of the burst frequency $f_1$ by a pulse cycle $T_1$ such that the duty ratio $d_1$ is included in the range of 5 to 50 [%], and the vibration frequency $f_2$ of the tool during the burst period such that the vibration frequency $f_2$ is included in the range of 20 to 60 [kHz].

According to this structure, the vibration device mounted on the housing vibrates the tool attached to the vibration device. The controller controls the vibration of the tool due to the vibration device such that the vibration is burst oscillation in which vibration and stop of vibration are repeated. Specifically, the controller controls the burst frequency $f_1$ of the tool such that the burst frequency $f_1$ is a low frequency in the range of 1 to 8 [Hz], whose cycle of a burst period and a stop period is recognizable for an operator. The controller further controls the duty ratio $d_1$, obtained by dividing the pulse width $t_1$ of the burst frequency by a pulse cycle $T_1$, such that the duty ratio $d_1$ is included in the range of 5 to 50 [%]. With the above, an operator can perceive a feeling of a hammer striking a chisel, so that the operator can cut a workpiece while accurately checking the approximation of the amount of cutting, or how much cutting has been made so far, from the cycle of striking at the burst frequency $f_1$ and a feeling of cutting strokes. This can improve the operability. It is possible to gradually and stepwisely insert the tool into a workpiece to a target depth while cutting the workpiece. Also, as the controller controls the vibration frequency $f_2$ of the tool during the burst period such that the vibration frequency $f_2$ is included in the range of 20 to 60 [kHz], it is possible to achieve accurate cutting with high-frequency vibration.

[2] It is preferred that, in the handpiece-type high-frequency vibration cutting device according to the preset invention, the controller may control the burst frequency $f_1$ such that the burst frequency $f_1$ is included in the narrow range of 1 to 4 [Hz], and the duty ratio $d_1$ such that the duty ratio $d_1$ is included in the narrow range of 10 to 25[%].

According to this structure, as the controller controls the burst frequency $f_1$ such that the burst frequency $f_1$ is included in the range of 1 to 4 [Hz] and the duty ratio $d_1$ such that the duty ratio $d_1$ is included in the narrow range of 10 to 25 [%], an operator can more readily recognize a cycle of a burst period and a stop period. Consequently, it is possible to give an operator a clearer feeling of sound, for example, similar to a sound to be made by striking a chisel with a hammer, so that the operator can readily recognize a feeling of cutting strokes, which can further improve the operability.

[3] It is preferred that, in the handpiece-type high-frequency vibration cutting device according to the preset invention, the housing, constituting the handpiece, may have an output unit configured to output sound or light toward an operator, and the controller may control the output unit such that the output unit outputs sound or light in a cycle one to fifty integer times as large as a cycle (1/f1) of the burst oscillation.

According to this structure, as the output unit that outputs sound or light is provided to the housing constituting the handpiece, an operator can readily recognize sound or light from outside. Then, as the controller controls the output unit such that the output unit outputs sound or light in a cycle one to fifty integer times as large as the cycle (1/f1) of the burst oscillation, the operator can approximate the amount of cutting, based on the interval between outputs of sound or light. That is, the operator can learn a more suitable feeling of cutting, which can further improve the operability.

[4] It is preferred that, in the handpiece-type high-frequency vibration cutting device according to the preset invention, the housing, constituting the handpiece, may have a vibrator configured to vibrate the housing under control by the controller, and the controller may control the vibrator such that the vibrator vibrates in a cycle one to fifty integer times as large as the cycle (1/f1) of the burst oscillation and in a direction perpendicular to a vibration direction of the vibration device.

According to this structure, as the vibrator that vibrates the housing is provided to the housing, which constitutes the handpiece, an operator can recognize the vibration of the housing. Then, as the controller controls the vibrator such that the vibrator vibrates in a cycle one to fifty integer times as large as the cycle (1/f1) of the burst oscillation and in a direction perpendicular to the vibration direction of the vibration device, an operator can perceive a feeling of cutting, based on the interval of such a subtle vibration of the housing that does not hinder cutting. That is, the operator can learn a more suitable feeling of cutting, which can further improve the operability.

BRIEF DESCRIPTION OF DRAWINGS

FIG. 3 is a diagram explaining the result of operation of a handpiece-type high-frequency vibration cutting device according to the present invention.

DESCRIPTION OF EMBODIMENTS

First Embodiment

Figure 1:
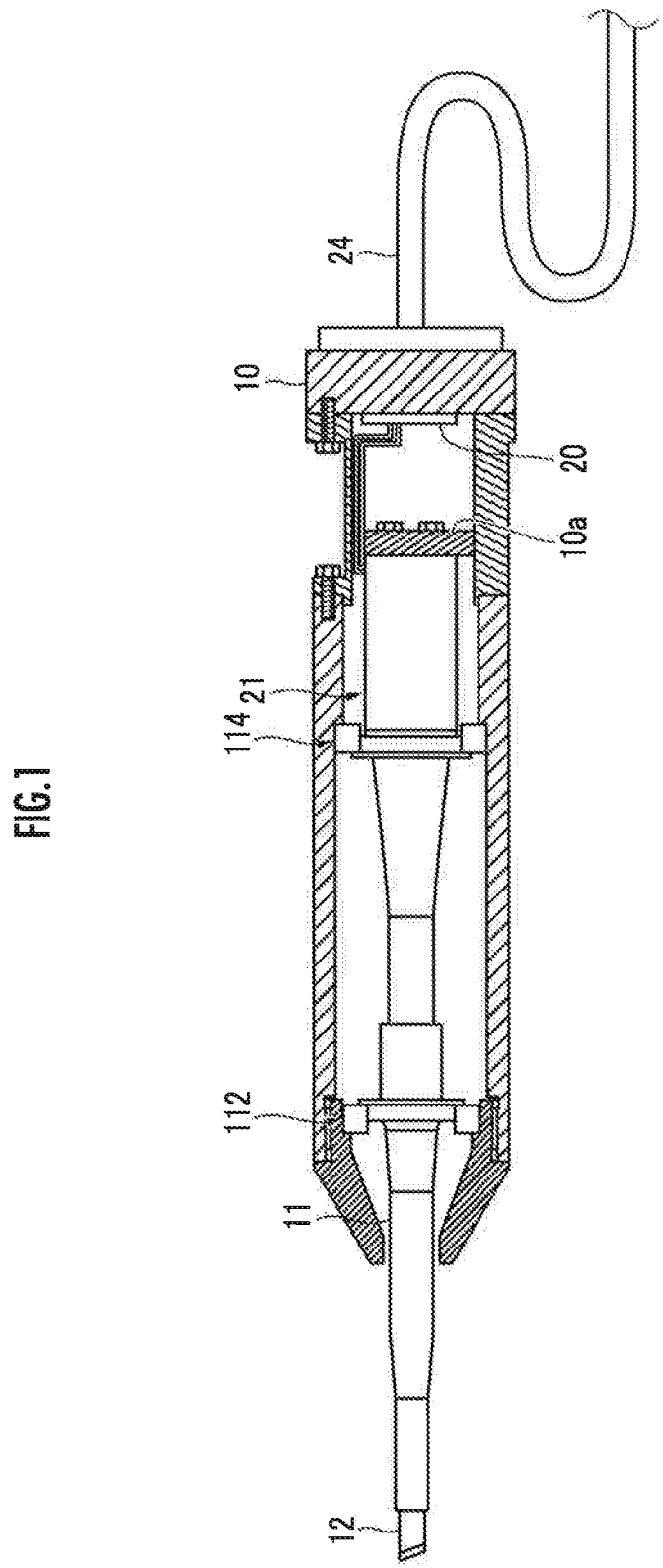
FIG. 1 is a diagram explaining a structure of a handpiece-type high-frequency vibration cutting device as a first embodiment of the present invention.

A handpiece-type high-frequency vibration cutting device according to a first embodiment of the present invention, illustrated in FIG. 1, includes a substantially cylindrical housing 10 that constitutes a handpiece, a holding member 11, a tool 12, a controller 20, and a vibration device 21.

The housing 10 is designed to have such a dimension that allows a standard-sized person to hold the housing 10 with its one hand. The handpiece for the high-frequency vibration cutting device includes structural components, such as the housing 10 and the holding member 11 that is at least partially disposed in the inside space of the housing 10. In view of reduction in weight of the handpiece to make a readily handleable handpiece, the kinds and designs of the respective structural components may be appropriately selected.

The rear end portion of the holding member 11 is attached to the vibration device 21. The holding member 11 is supported via support portions 112, 114, which are secured on the inside wall of the housing 10, so as to freely move in the axial direction of the housing 10. The holding member 11 has a function as a horn that increases an amplitude. The tool 12 is removably attached to the tip end portion of the holding member 11. The dimension of the tool 12 in a direction perpendicular to the axial direction of the holding member 11 is included in the range of 1 to 10 [mm] or 2 to 5 [mm], for example. As the shape of the tool 12, any shapes such as a cutter having a linear or arc tip end portion or a substantially cylindrical, spoon-like, bent, or curved rod are employed.

The vibration device 21 is mounted on a mount portion 10a of the housing 10, and includes piezoelectric elements disposed in the inside space of the housing 10. The vibration device 21 causes the holding member 11 to vibrate or move in a reciprocating manner in the axial direction of the holding member 11. A cable 24 is attached to the rear end portion of the housing 10, and the controller 20 and a conducting wire are disposed in the inside space of the housing 10. The vibration device 21 is fed with power via the cable 24, the controller 20, and the conducting wire.

The vibration device 21 and the holding member 11 are disposed so as to have a common axial line and be spaced apart from each other in a direction of their axial line. With the above, the space occupied by the vibration device 21 and the holding member 11 in the inside space of the housing 10 in a direction perpendicular to the axial line, and thus the housing 10, can be made compact, compared with a case in which the axial lines are defined spaced apart from each other so as to be parallel or non-parallel to each other. With the above, a high-frequency vibration cutting device can be implemented as a handpiece that can be readily held and is improved in operability.

As a force from the vibration device 21 is directly transmitted to the holding member 11 without use of a transmission mechanism, lubricant agent, such as grease, which is generally used for a transmission mechanism, is unnecessary. Accordingly, in the case where a handpiece-type high-frequency vibration cutting device as medical equipment is sterilized with high pressure vapor, contamination of the medical equipment attributed to the presence of lubricant agent is avoided.

The controller 20 controls the operation of the vibration device 21. The controller 20 includes a microcomputer or a processor, which is disposed in the inside space of the housing 10 together with a board where the microcomputer or the processor is mounted. The controller 20 controls the vibration frequency f2 of the tool 12 in the axial direction via the holding member 11 due to the vibration device 21 such that the vibration frequency f2 is included in the range of 20 to 60 [kHz]. More preferably, the vibration frequency f2 is controlled such that f2=25 to 35 [kHz].

Further, the controller 20 controls the vibration of the tool 12 caused by the vibration device 21 such that the vibration is burst oscillation in which vibration and stop of vibration are repeated. Further, the controller 20 controls the burst frequency f1 of the tool 12, whose one cycle consists of a burst period with the tool 12 vibrating and a stop period with the tool 12 not vibrating, such that the burst frequency f1 has a low frequency as a whole whose cycle of a burst period and a stop period is recognizable for an operator.

According to the handpiece-type high-frequency vibration cutting device having the above-described structure, the holding member 11 is driven to move in a reciprocating manner in its axial direction, whereby an object is cut with the tool 12 attached to the tip end portion of the holding member 11.

The controller 20 controls the vibration of the tool 12 caused by the vibration device 21 such that the vibration is burst oscillation in which vibration and stop of vibration are repeated.

Specifically, the controller 20 controls the burst frequency f1 of the tool 12 such that the burst frequency f1 is a low frequency in the range of 1 to 8 [Hz], whose cycle of a burst period and a stop period is recognizable for an operator. The controller 20 further controls the duty ratio d1, obtained by dividing the pulse width t1 of the burst frequency by a pulse cycle T1, such that the duty ratio d1 is included in the range of 5 to 50 [%]. With the above, an operator is given a feeling of sound like a sound to be made by striking a chisel with a hammer, so that the operator can cut a workpiece while accurately checking the approximation of the amount of cutting, or how much cutting has been made so far, based on the cycle of strokes at the burst frequency f1 and a feeling of cutting strokes caused by the strokes. This enables improvement in operability and also gradual and stepwise insertion of the tool into the workpiece to a target depth while cutting the workpiece.

For more preferable frequencies, the controller 20 controls the vibration frequency f2 of the tool 12 during a burst period such that the vibration frequency f2 is included in the range of 20 to 60 [kHz], the burst frequency f1 such that the burst frequency f1 is included in the range of 1 to 4 [Hz], and the duty ratio d1 such that the duty ratio d1 is included in the narrow range of 10 to 25 [%].

Below, a result of operation of the tool 12 of the handpiece-type high-frequency vibration cutting device in vibration at the vibration frequency f2 will be described. As the controller 20 controls the vibration frequency f2 of the tool 12 during a burst period such that the vibration frequency f2 is included in the range of 20 to 60 [kHz], it is possible to achieve accurate cutting with high-frequency vibration.

Below, a result of operation of the tool 12 of the handpiece-type high-frequency vibration cutting device in vibration at the burst frequency f1 will be described. FIG. 3 illustrates results about a feeling of cutting perceived by an operator and a feeling of fully-stopped cutting perceived by the operator with respect to the burst frequency f1. Specifically, while stepwisely changing the burst frequency f1 from 0.1 [Hz] to 14 [Hz], a feeling of cutting perceived by an operator is rated with x for a bad result, a triangle for a poor result, a circle for a good result, and a double-circle for a better result. Ð

As to a feeling of cutting perceived by an operator, results with the burst frequency f1 at 0.5 [Hz] or 5 [Hz] to 8 [Hz] are good, and those with the burst frequency f1 at 1 [Hz] to 4 [Hz] are better.

As to a feeling of fully-stopped cutting perceived by an operator, or a feeling which an operator feels as if cutting were fully stopped, a result with the burst frequency f1 at 0.5 [Hz] is poor, and those at 1 [Hz] to 14 [Hz] are good.

The above-described results show that, as a low burst frequency f1 is controlled such that the burst frequency f1 is included in the range of 1 to 8 [Hz], an operator can avoid erroneous recognition that cutting is fully stopped when the burst frequency f1 is 1 [Hz] or greater, and can recognize a cycle of a burst period and a stop period when the burst frequency f1 is 8 [Hz] or less.

Further, the controller 20 controls the burst frequency f1 such that the burst frequency f1 is included in the range of 1 to 4 [Hz], and the duty ratio d1 such that the duty ratio d1 is included in the narrow range of 10 to 25 [%]. With the above, an operator can avoid erroneous recognition that cutting is fully stopped when the burst frequency f1 is 1 [Hz] or greater, and can more readily distinguish a burst period and a stop period when the burst frequency f1 is 4 [Hz] or less. Further, as the duty ratio d1 is controlled such that the duty ratio d1 is included in the narrow range of 10 to 25[%], it is possible to have an operator learn a more suitable feeling of cutting to thereby further improve the operability. Consequently, it is possible to give an operator a clearer feeling of sound, for example, like a sound to be made by striking a chisel with a hammer so that the operator can more readily perceive a feeling of cutting strokes to thereby further improve the operability.

Figure 4A:
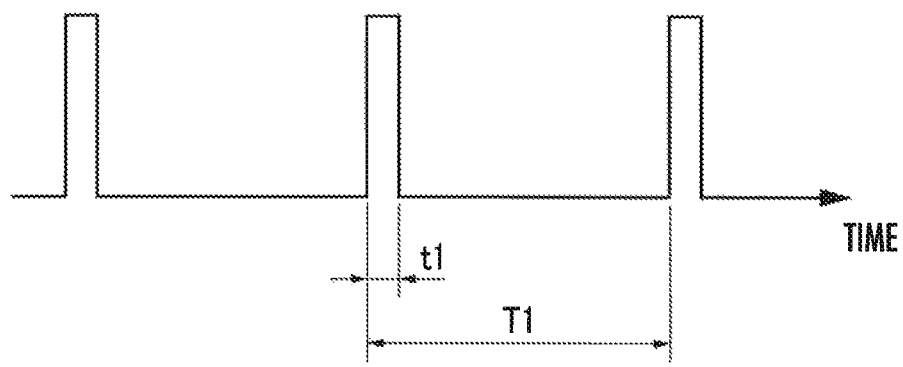
FIG. 4A is a diagram explaining the waveform of a burst frequency modulated into a rectangular wave as a whole according to the present invention.

Below, the waveform of a burst wave will be described. FIG. 4A is a diagram explaining the waveform of a burst frequency that has been modulated into a rectangular wave as a whole according to an embodiment of the present invention, in which a burst period t1 with the tool 12 (refer to FIG. 1) vibrating and a stop period (T141) with the tool 12 not vibrating together make one cycle T1. The duty ratio d1 is a value obtained by dividing the pulse width t1 of the burst frequency by a pulse cycle T1.

The controller 20 (refer to FIG. 1) controls the vibration device 21 such that the vibration device 21 vibrates at such a high frequency that makes the vibration frequency f2 in the axial direction of the holding member 11 due to the vibration device 21 (refer to FIG. 1) included in the range of 20 to 60 [kHz], for example, and such that the burst wave is modulated into a rectangular wave as a whole. The burst wave as a whole is controlled by the controller 20 such that the burst frequency f1 is included in the range of 1 to 8 [Hz], and such that the duty ratio d1 is included in the range of 5 to 50 [%].

In FIG. 4A, a burst wave is modulated into a rectangular wave as a whole. With the above, an operator can recognize a feeling of cutting strokes like strokes to be made by striking the tool 12 with a hammer.

Figure 4B:
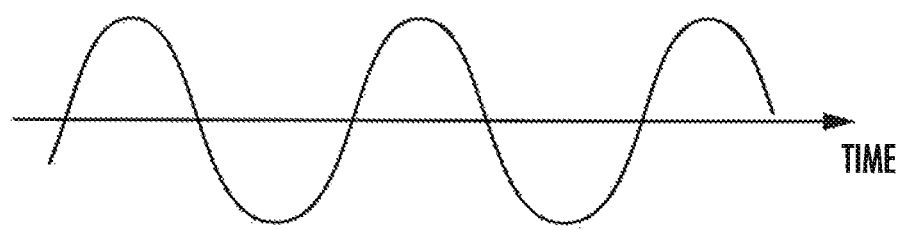
FIG. 4B is a diagram explaining the waveform of a burst frequency modulated into a sin wave as a whole in a comparative example.

Below, the waveform of a burst wave in a comparative example will be described. FIG. 4B is a diagram explaining the waveform of a burst frequency modulated into a sin wave as a whole in a comparative example. Although the burst wave itself has a high frequency, the waveform of the burst wave as a whole is that of a sin wave attributed to a supersonic modulated so as to have a low frequency. With the above, an operator cannot perceive a difference between a stop period and a vibration period of the tool from the burst wave as a whole, and thus cannot recognize a feeling of cutting strokes.

Figure 5A:
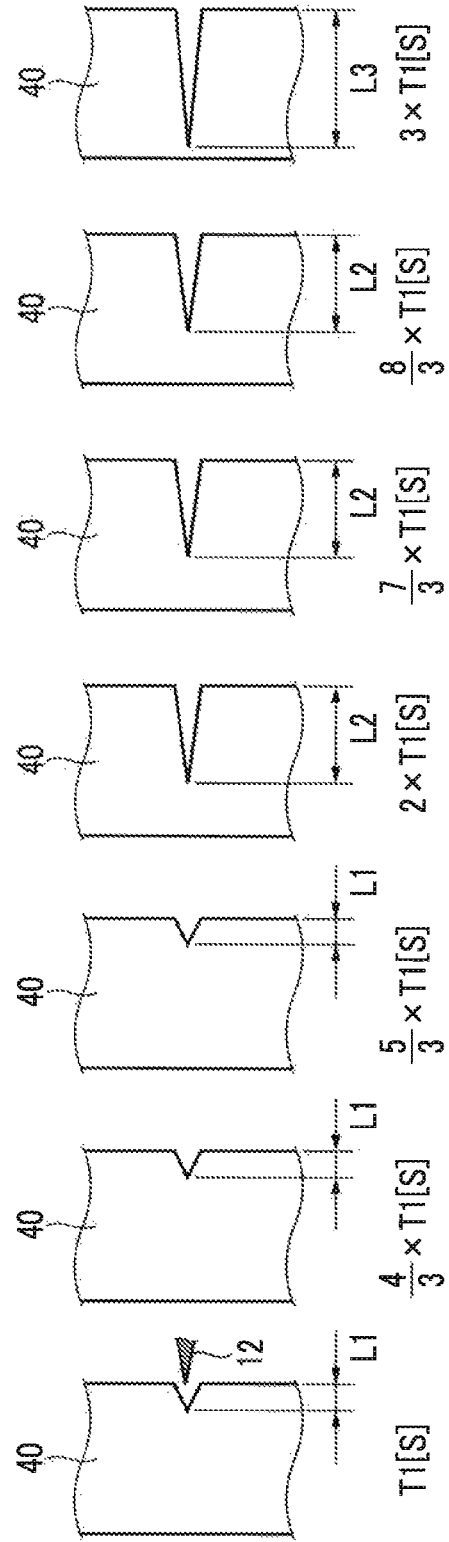
FIG. 5A is a diagram explaining an elapse of time and a cutting state of a workpiece according to the present invention.

Below, an elapse of time and a cutting state of a workpiece will be described. FIG. 5A is a diagram explaining an elapse of time and a cutting state of a workpiece in an embodiment according to the present invention. With an elapse of time T1[s] after the start of cutting, a workpiece 40 has been cut by a cutting amount L1 with the tool 12. With an elapse of time of (4/3)×T1[s] and of time of (5/3)×T1[s], no further cutting is made, so that the cutting amount remains as L1.

With an elapse of time of 2×T1[s], the workpiece 40 has been further cut with the tool 12, so that the cutting amount L2 is resulted. With an elapse of time of (7/3)×T1[s] and of time of (8/3)×T1[s], no further cutting is made, so that the cutting amount remains as L2.

With an elapse of time of 3×T1[s], the workpiece 40 has been further cut with the tool 12 until the cutting amount L3 is resulted. As described above, it is possible to insert the tool 12 gradually and stepwisely into the workpiece 40 to a target depth while cutting the workpiece 40. An operator can recognize a feeling of cutting strokes like ones to be made by striking the tool 12 with a hammer, and thus can cut the workpiece 40 while accurately checking the approximation of the amount of cutting, or how much cutting has been made so far, from the cycle of strokes at the burst frequency f1 and an accompanying feeling of cutting strokes. This enables improvement in operability.

Figure 5B:
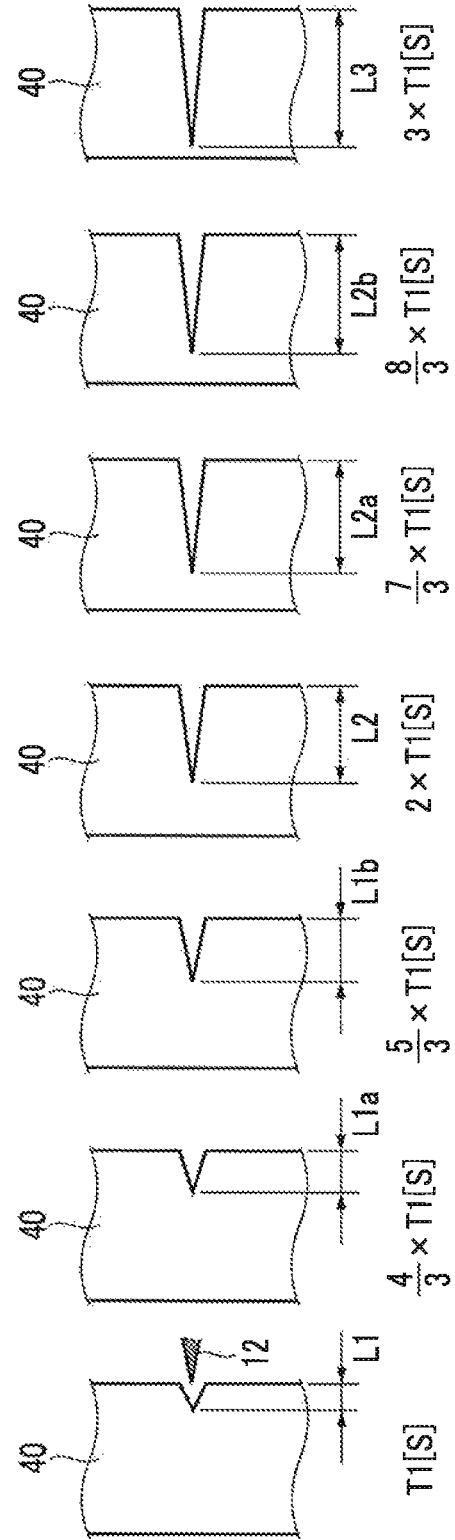
FIG. 5B is a diagram explaining an elapse of time and a cutting state of a workpiece in a comparative example.

Below, an elapse of time and a cutting state of a workpiece in a comparative example will be described. FIG. 5B is a diagram explaining an elapse of time and a cutting state of a workpiece in the comparative example. With an elapse of time T1[s] after the start of cutting, the workpiece 40 has been cut by a cutting amount L1 with the tool 12. With an elapse of time of (4/3)×T1[s], the workpiece 40 has been further cut until the cutting amount L1a is resulted. With an elapse of time of (5/3)×T1[s], the workpiece 40 has been further cut until the cutting amount L1b is resulted.

With an elapse of time of 2×T1[s], the workpiece 40 has been further cut with the tool 12 until the cutting amount L2 is resulted. With an elapse of time of (7/3)×T1[s], the workpiece 40 has been further cut until the cutting amount L2a is resulted. With an elapse of time of (8/3)×T1[s], the workpiece 40 has been further cut until the cutting amount L2b is resulted.

With an elapse of time of 3×T1[s], the workpiece 40 has been further cut with the tool 12 until the cutting amount L3 is resulted. As described above, in the comparative example, as the amount of cutting smoothly increases in proportion to an elapse of time, it is not possible to recognize a feeling of cutting strokes.

Figure 6A:
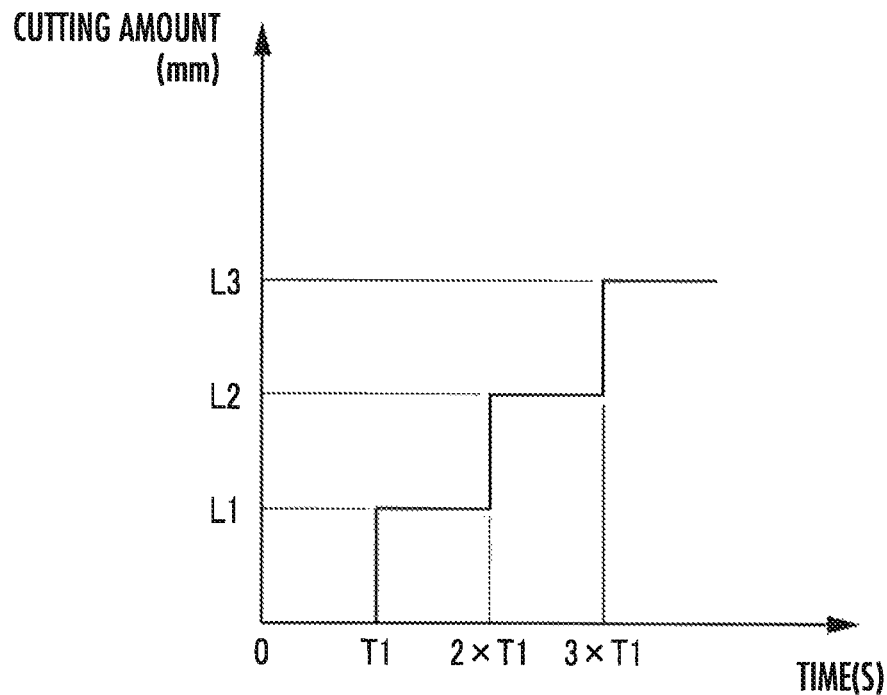
FIG. 6A is a diagram relevant to an elapse of time and an amount of cutting according to the present invention.

Below, an elapse of time and an amount of cutting will be described referring to graphs. FIG. 6A is a diagram relevant to an elapse of time and an amount of cutting according to an embodiment of the present invention, in which the amount of cutting increases stepwisely, for example, from L1, L2, to L3, for every elapse of a burst cycle T1, for example, from burst cycles T1, 2×T1, to 3×T1.

Figure 6B:
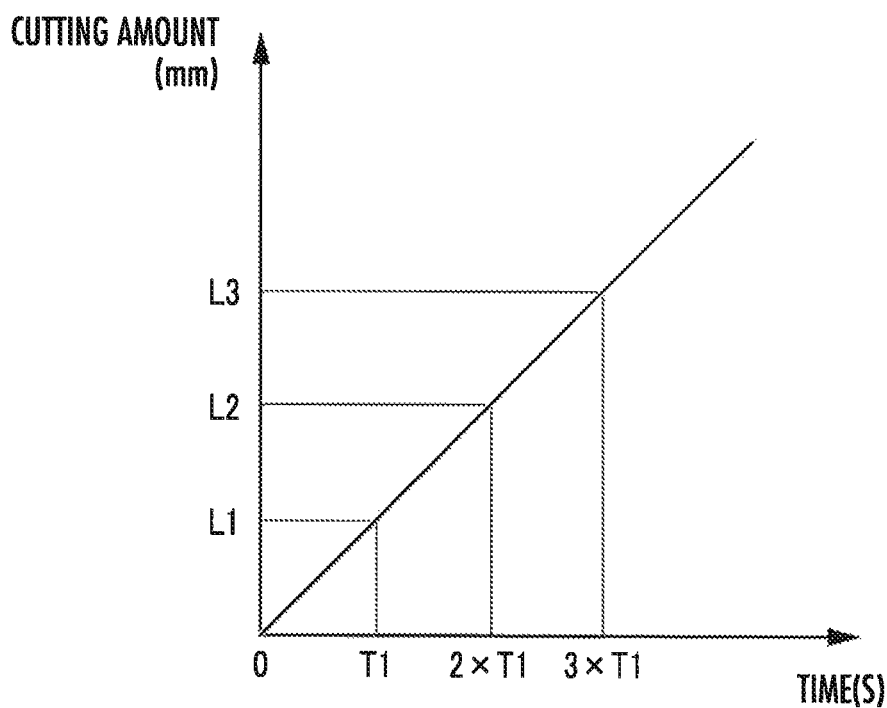
FIG. 6B is a diagram relevant to an elapse of time and an amount of cutting in a comparative example

In contrast, FIG. 6B is a diagram relevant to an elapse of time and an amount of cutting in a comparative example, in which the amount of cutting increases linearly and proportionally, for example, from L1, L2, to L3, as time elapses, for example, from T1, 2×T1, to 3×T1.

Second Embodiment

Figure 2:
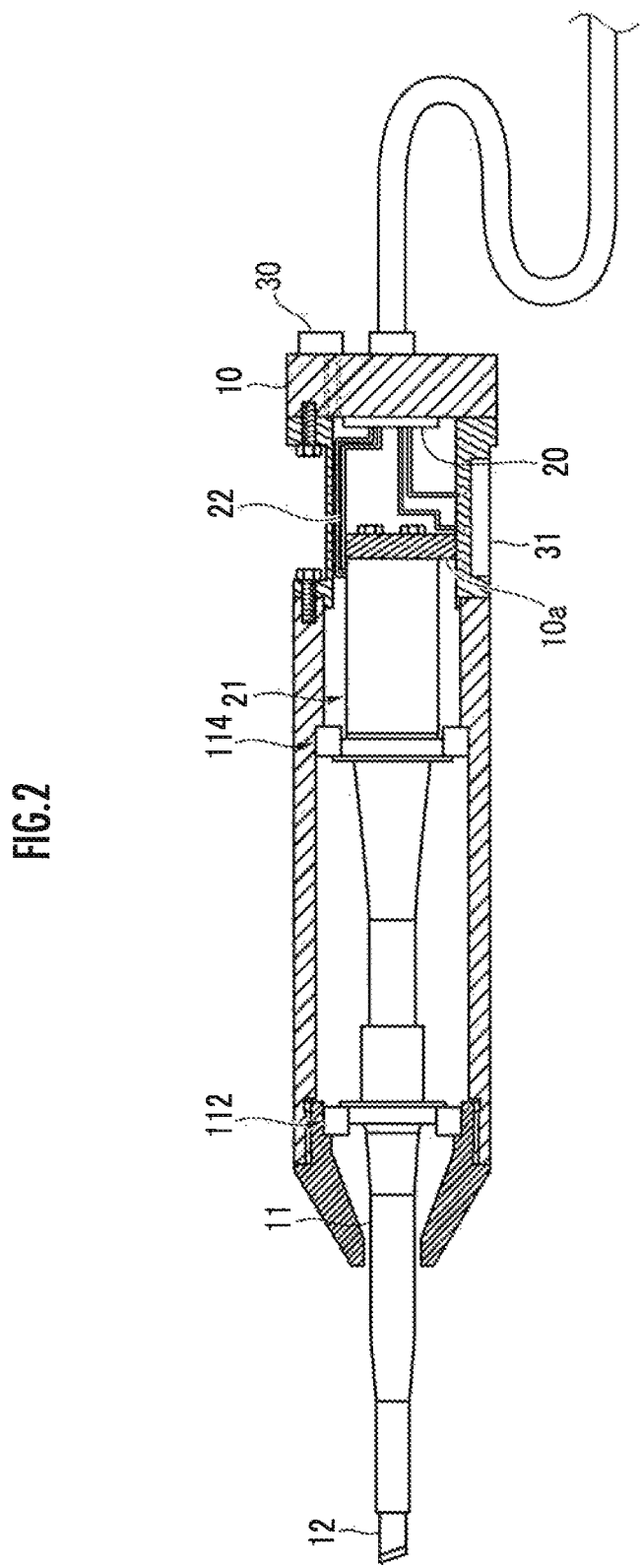
FIG. 2 is a diagram explaining a structure of a handpiece-type high-frequency vibration cutting device as a second embodiment of the present invention.

Below, a second embodiment of the present invention will be described. Note that descriptions on structural components similar to those in the first embodiment are omitted, with the same reference numerals used. As illustrated in FIG. 2, a handpiece-type high-frequency vibration cutting device according to a second embodiment of the present invention includes an output unit 30 at the rear end portion of the housing 10 and a vibrator 31 on the outer circumferential portion of the housing 10. The output unit 30 and the vibrator 31 are fed with electric power from the cable 24 as being connected via the controller 20. Further, the output unit 30 and the vibrator 31 are connected to the controller 20 via a wire (not illustrated) and subjected to restriction on their outputs by the controller 20.

The output unit 30 is a small-sized speaker that outputs sound. The controller 20 controls the output unit 30 such that the output unit 30 outputs sound or light in a cycle one to fifty integer times as large as the cycle (1/f1) of the burst oscillation. Accordingly, an operator can audibly approximate the amount of cutting, based on the interval between outputs of sound. That is, an operator can learn a more suitable feeling of cutting, and the operability can thus be further improved.

Note that matching the frequency f3 at which the output unit 30 outputs sound with the burst frequency f1 can make a feeling of cutting more readily perceivable, and thus to further improve the operability.

Note that although the output unit 30 is a speaker in this embodiment, the output unit 30 may be a light source that outputs light. The controller 20 controls the output unit 30 such that the output unit 30 outputs light in a cycle one to fifty integer times as large as the cycle (1/f1) of the burst oscillation. In the case where the output unit 30 is a light source, an extent of cutting can be visually recognized. This enables improvement in operability of the handpiece-type high-frequency vibration cutting device.

As described above, since the output unit 30 that outputs sound or light is mounted on the housing 10 of the handpiece, an operator can readily recognize sound or light from outside. Further, since the controller 20 controls the output unit such that the output unit outputs sound or light at a predetermined interval, an operator can approximate the amount of cutting, based on the interval between outputs of sound or light. This can give an operator a more suitable feeling of cutting, and thus further improve the operability.

Also, since the vibrator 31 that vibrates the housing 10 is mounted on the housing 10, which constitutes a handpiece, an operator can be aware of such a subtle vibration of the housing 10 that does not hinder cutting. In this case, preferably, the controller 20 controls the vibrator 31 such that the vibrator 31 vibrates in a cycle one to fifty integer times as large as the cycle (1/f1) of the burst oscillation and in a direction perpendicular to the vibration direction of the vibration device 21. An operator can perceive a feeling of cutting, based on the interval of vibration of the housing 10. That is, a more suitable feeling of cutting can be transmitted to an operator, to thereby further improve the operability. Further, matching the frequency f4 of the vibration of the vibrator 31 with the burst frequency f1 can make a feeling of cutting more readily perceivable to thereby further improve the operability.

Note that the high-frequency vibration cutting device may further include an input interface via which a user inputs the type of the tool 12, so that the controller 20 adjusts a combination of the vibration frequency f2 and the rotation speed v of the tool 12, depending on the type of tool inputted via the input interface. For example, the input interface may include, for example, a keyboard, a touch panel button, or an operation button.

Also, the vibration device 21, the output unit (a speaker, a light source) 30, and the vibrator 31 may be selectively controlled. Also, the high-frequency vibration cutting device may include one or more of the vibration device 21, the output unit (a speaker, a light source) 30, and the vibrator 31.

Also, although the controller 20 controls an output from the output unit 30 and vibration of the vibrator 31 such that these have a cycle one to fifty integer times as large as the cycle (1/f1) of the burst oscillation in the embodiment, this is not exclusive, and the output and the vibration can be controlled so as to have such a cycle that gives an operator a feeling of comfortableness, or so-called (1/f) fluctuation, or a cycle that allows an operator to know the approximation of the amount of cutting.

DESCRIPTION OF REFERENCE NUMERALS

10 housing
11 holding member
12 tool
20 controller
21 vibration device
30 output unit
31 vibrator

The invention claimed is:

1. A handpiece-type high-frequency vibration cutting device, comprising:
   a housing;
   a vibration device mounted on the housing;
   a tool mounted on the vibration device; and
   a controller disposed inside of the housing and configured to control an operation of the vibration device to thereby cause the tool to vibrate in a direction of an axial line of the vibration device,
   wherein
   the controller is operable to control vibration of the tool, the vibration being caused by the vibration device, such that the vibration is burst oscillation in which vibration and stop of vibration are repeated, and
   the controller is operable to control a burst frequency f1 of the tool such that the burst frequency f1 as a whole is included in a range of 1 to 8 Hz, one cycle of the burst frequency f1 including a burst period with the tool vibrating and a stop period with the tool not vibrating, a duty ratio d1 obtained by dividing a pulse width t1 of the burst frequency f1 by a pulse cycle T1 such that the duty ratio d1 is included in a range of 5 to 50%, and a vibration frequency f2 of the tool during the burst period such that the vibration frequency f2 is included in a range of 20 to 60 kHz.

2. The handpiece-type high-frequency vibration cutting device according to claim 1, wherein the controller is operable to control the burst frequency f1 such that the burst frequency f1 is included in a narrow range of 1 to 4 Hz, and the duty ratio d1 such that the duty radio d1 is included in a narrow range of 10 to 25%.

3. A handpiece-type high-frequency vibration cutting device, comprising:
   a housing;
   a vibration device mounted on the housing;
   a tool mounted on the vibration device; and
   a controller configured to control an operation of the vibration device to thereby cause the tool to vibrate in a direction of an axial line of the vibration device,
   wherein:
   the controller is operable to control vibration of the tool, the vibration being caused by the vibration device, such that the vibration is burst oscillation in which vibration and stop of vibration are repeated,
   the controller is operable to control a burst frequency f1 of the tool such that the burst frequency f1 as a whole is included in a range of 1 to 8 Hz, one cycle of the burst frequency f1 including a burst period with the tool vibrating and a stop period with the tool not vibrating, a duty ratio d1 obtained by dividing a pulse width t1 of the burst frequency f1 by a pulse cycle T1 such that the duty ratio d1 is included in a range of 5 to 50%, and a vibration frequency f2 of the tool during the burst period such that the vibration frequency f2 is included in a range of 20 to 60 kHz,
   the housing, constituting a handpiece, has an output unit configured to output sound or light toward an operator, and
   the controller is operable to control the output unit such that the output unit outputs sound or light in a cycle one to fifty integer times as large as a cycle (1/f1) of the burst oscillation.

4. A handpiece-type high-frequency vibration cutting device, comprising:
   a housing;
   a vibration device mounted on the housing;
   a tool mounted on the vibration device; and
   a controller configured to control an operation of the vibration device to thereby cause the tool to vibrate in a direction of an axial line of the vibration device,
   wherein:
   the controller is operable to control vibration of the tool, the vibration being caused by the vibration device, such that the vibration is burst oscillation in which vibration and stop of vibration are repeated,
   the controller is operable to control a burst frequency f1 of the tool such that the burst frequency f1 as a whole is included in a range of 1 to 8 Hz, one cycle of the burst frequency f1 including a burst period with the tool vibrating and a stop period with the tool not vibrating, a duty ratio d1 obtained by dividing a pulse width t1 of the burst frequency f1 by a pulse cycle T1 such that the duty ratio d1 is included in a range of 5 to 50%, and a vibration frequency f2 of the tool during the burst period such that the vibration frequency f2 is included in a range of 20 to 60 kHz,
   the housing, constituting the handpiece, has a vibrator configured to vibrate the housing under control by the controller, and
   the controller is operable to control the vibrator such that the vibrator vibrates in a cycle one to fifty integer times as large as the cycle (1/f1) of the burst oscillation and in a direction perpendicular to a vibration direction of the vibration device.

* * * * *